(12) United States Patent  
Aradi et al.

(10) Patent No.: US 8,241,599 B2
(45) Date of Patent: Aug. 14, 2012

(54) METHOD OF USING VOLATILE ORGANOMETALLICS AS BIOMASS GASIFICATION CATALYSTS

(75) Inventors: Allen Aradi, Glen Allen, VA (US); Joseph Roos, Mechanicsville, VA (US); Tze-Chi Jao, Glen Allen, VA (US)

(73) Assignee: Afton Chemical Corporation, Richmond, VA (US)

( * ) Notice: Subject to any disclaimer, the term of this patent is extended or adjusted under 35 U.S.C. 154(b) by 266 days.

(21) Appl. No.: 12/475,664

(22) Filed: Jun. 1, 2009

(65) Prior Publication Data
US 2010/0303705 A1 Dec. 2, 2010

(51) Int. Cl.
*C01B 31/18* (2006.01)
*C01B 3/38* (2006.01)

(52) U.S. Cl. ..................... 423/418.2; 252/373
(58) Field of Classification Search .................. 423/650
See application file for complete search history.

(56) References Cited

U.S. PATENT DOCUMENTS

| | | | | |
|---|---|---|---|---|
| 6,898,936 B1 * | 5/2005 | Ochs et al. | .................. | 60/649 |
| 7,094,274 B2 * | 8/2006 | Aradi et al. | .................. | 95/58 |
| 7,416,716 B2 * | 8/2008 | Allam et al. | .................. | 423/437.1 |
| 7,736,402 B2 * | 6/2010 | Crorey, Jr. | .................. | 48/197 R |
| 2002/0155062 A1 * | 10/2002 | Lightner | .................. | 423/652 |
| 2005/0044778 A1 | 3/2005 | Orr | | |
| 2005/0257724 A1 * | 11/2005 | Guinther et al. | .................. | 110/345 |
| 2006/0175230 A1 | 8/2006 | Zhou et al. | | |
| 2007/0007121 A1 | 1/2007 | Guo et al. | | |
| 2007/0180760 A1 | 8/2007 | Zhou et al. | | |
| 2007/0225383 A1 | 9/2007 | Cortright et al. | | |
| 2008/0040969 A1 | 2/2008 | Aradi et al. | | |
| 2008/0103344 A1 | 5/2008 | Jones et al. | | |
| 2009/0071067 A1 * | 3/2009 | Macpherson et al. | .................. | 44/601 |
| 2009/0126433 A1 | 5/2009 | Piskorz et al. | | |
| 2009/0266081 A1 * | 10/2009 | Graham | .................. | 60/780 |
| 2009/0275787 A1 * | 11/2009 | Forster et al. | .................. | 568/903 |
| 2010/0076238 A1 | 3/2010 | Brandvold et al. | | |

FOREIGN PATENT DOCUMENTS

JP 2001-240877 * 9/2001

OTHER PUBLICATIONS

International Search Report and Written Opinion for PCT/US2010/031858, dated Jun. 29, 2010.
Guaiacyl and Syringyl Lignin Composition in Hardwood Cell Components; John R. Obst; Holzforschunh 36 (1982); pp. 143-152.
Office Action in U.S. Appl. No. 12/685,791, mail date Oct. 31, 2011.

* cited by examiner

*Primary Examiner* — Melvin C Mayes
*Assistant Examiner* — Kenneth Vaden
(74) *Attorney, Agent, or Firm* — Thomas & Karceski, PC

(57) ABSTRACT

The present invention relates to a method for improving biomass gasification. By the present invention, volatile organometallics are contacted with a biomass before or during gasification. By this method, the biomass improves gas yields while reducing solid (tar) and liquid yields. In addition, the volatile organometallics interact with lignin in the biomass to produce methanol, which, in turn, results in a stable liquid or oil by-product or otherwise stabilizes the gasification process of the biomass. The presently disclosed method can also lead to increased syngas production and is potentially $CO_2$ neutral. The energy input to the gasification is correspondingly reduced to reduce costs and the environmental impact associated with the gasification process.

39 Claims, 6 Drawing Sheets

Coniferyl alcohol

↓

Guaiacyl lignin

Synapyl alcohol

↓

Syringyl lignin

Hybrid Poplar Lignin Component

MMT Performance as a Biomass Gasification Catalyst

| Catalyst | Temp. (°C) | Oil yield (%) | Char Yield (%) | Gas yield (%) |
|---|---|---|---|---|
| Baseline | 450 | 43.70 | 14.90 | 41.50 |
| mmt® at 1.0% | 400 | 34.75 | 11.35 | 53.94 |
| mmt® at 4.0% | 400 | 25.50 | 11.09 | 63.41 |
| mmt® at 1.0% | 600 | 25.20 | 13.10 | 61.70 |
| mmt® at 1.0% | 800 | 5.90 | 6.50 | 87.60 |

FIGURE 2

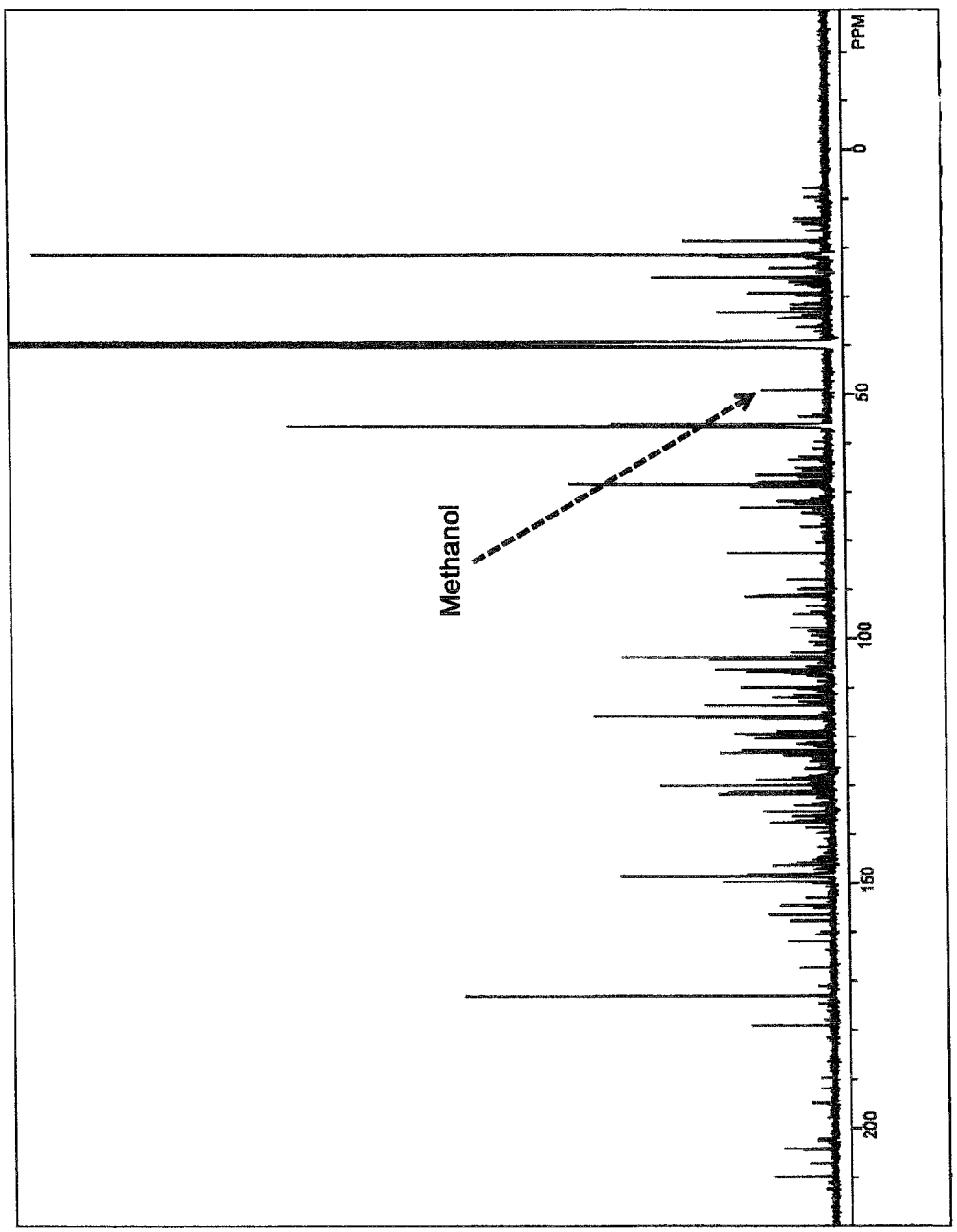
FIGURE 3: The $^{13}$Cnmr spectrum of the bio oil (w/o catalysts) obtained at 450°C

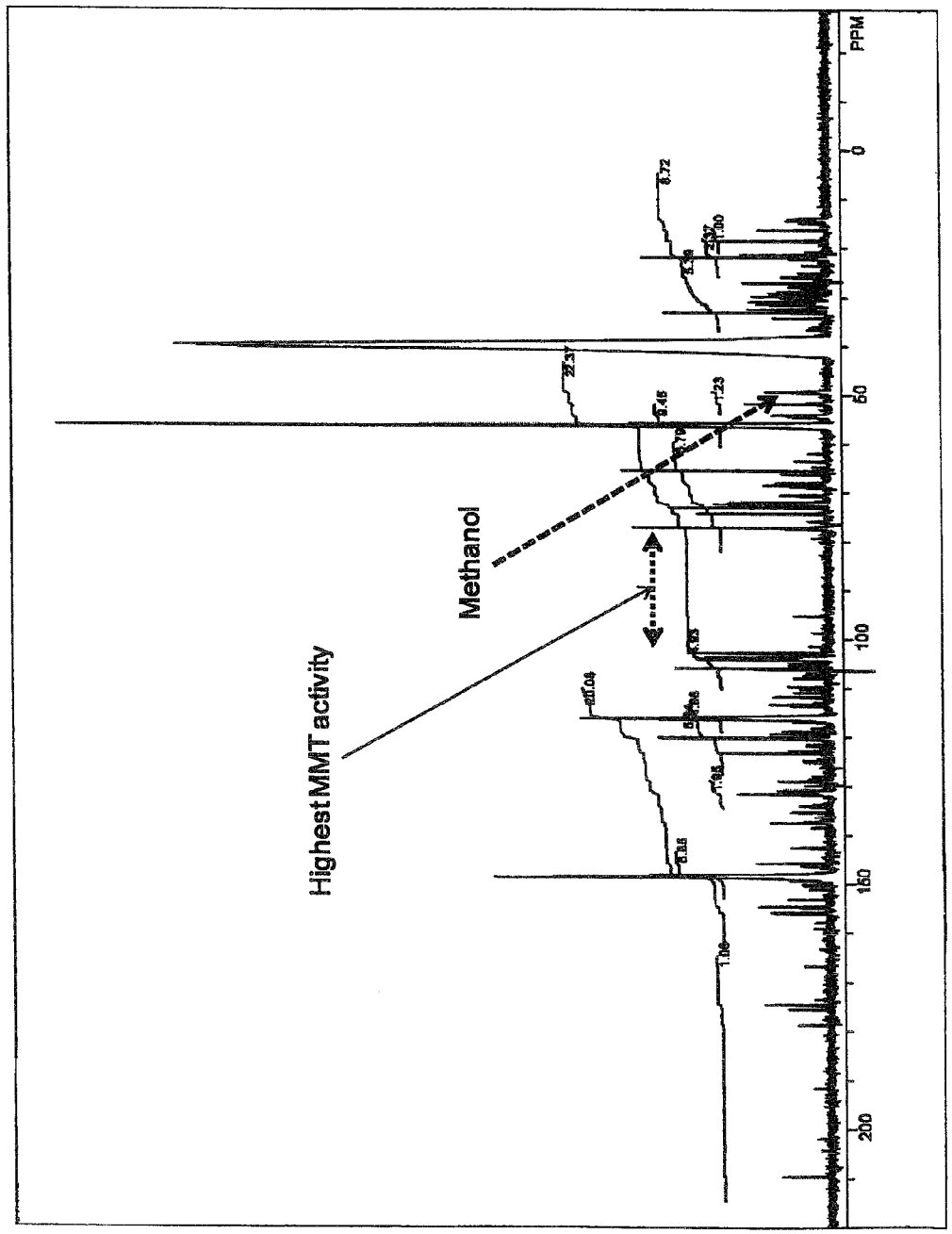
FIGURE 4: The $^{13}C$nmr spectrum of the bio oil obtained at 400°C

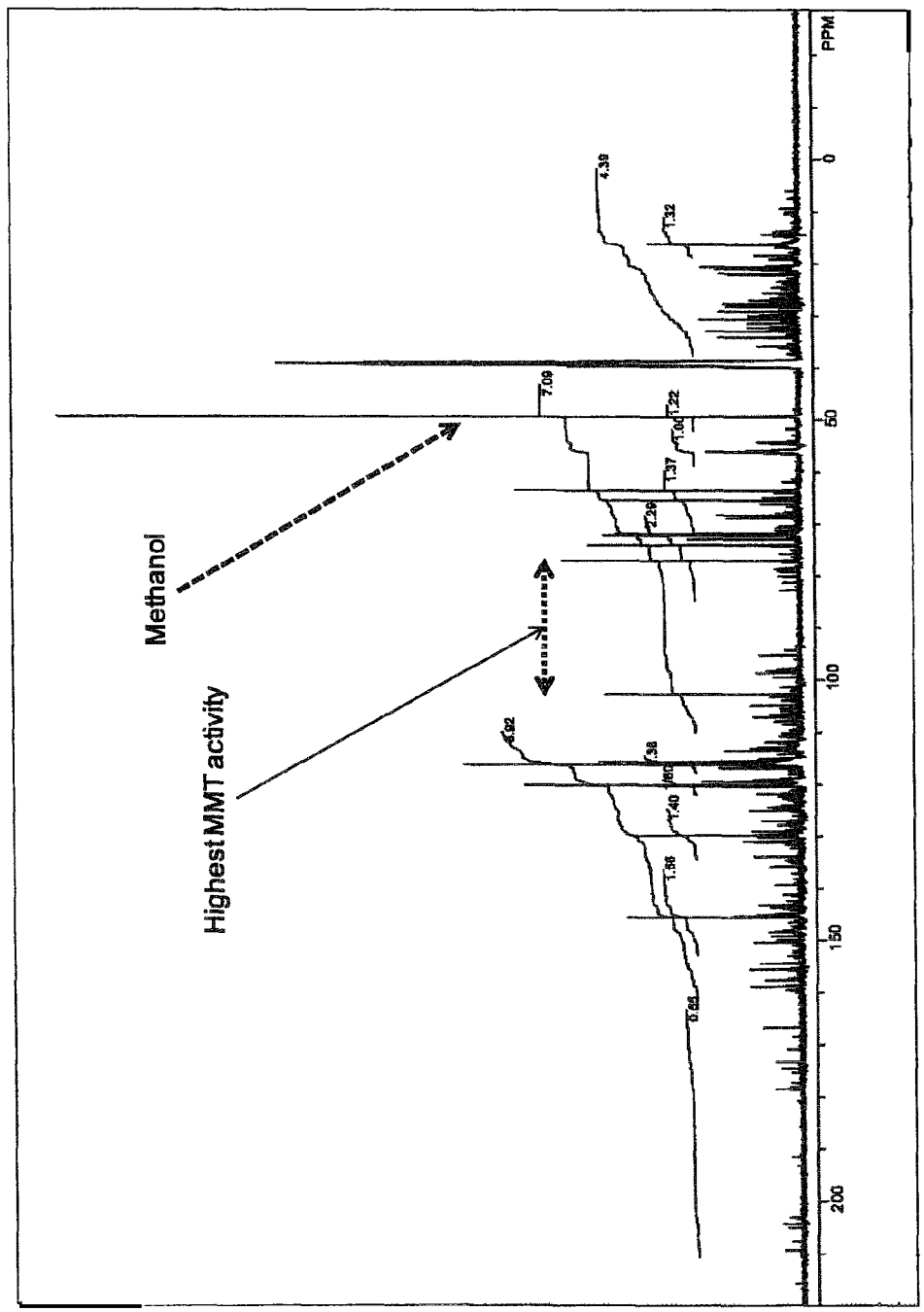
FIGURE 5: The $^{13}$Cnmr spectrum of the bio oil obtained at 600°C

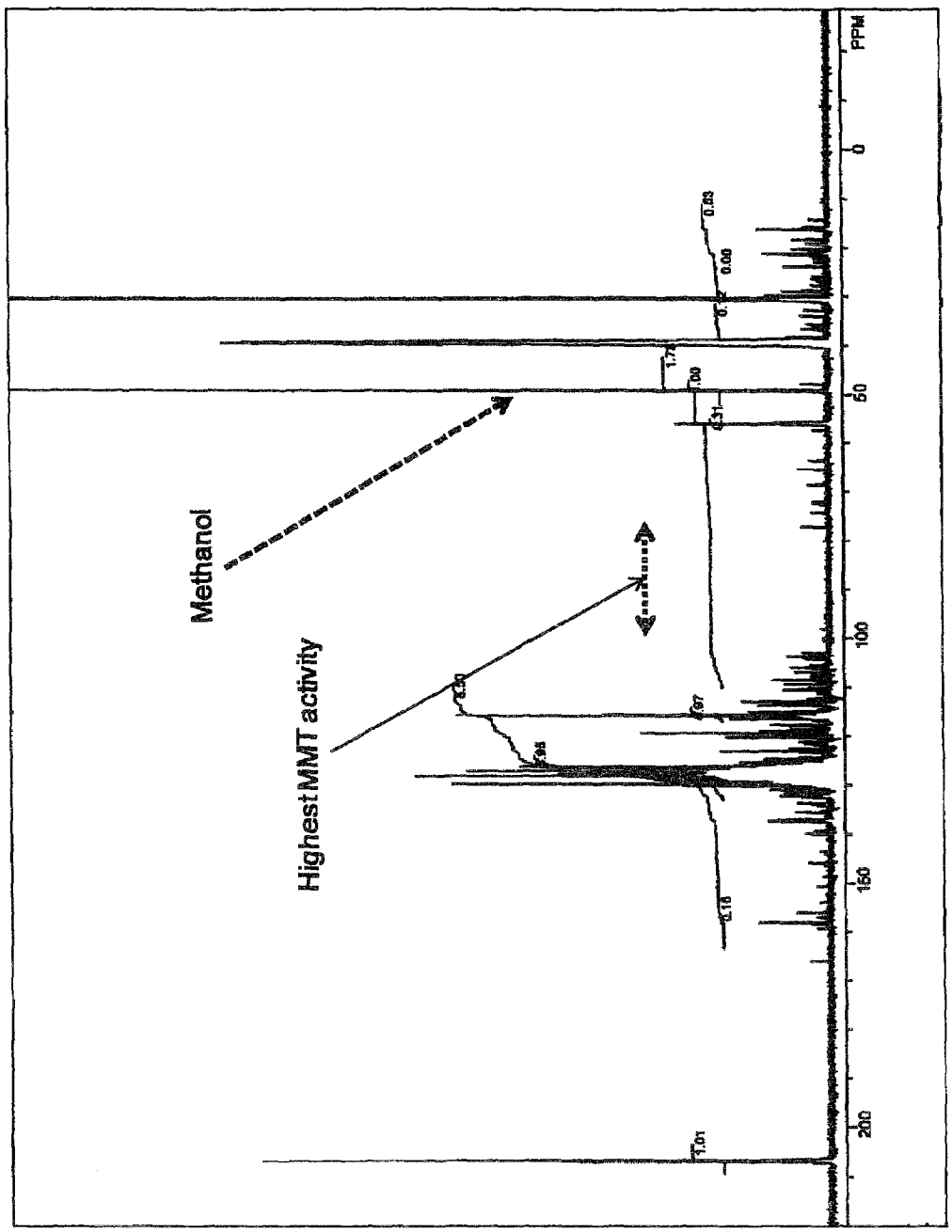
FIGURE 6: The $^{13}C$ nmr spectrum of the bio oil obtained at 800°C

METHOD OF USING VOLATILE ORGANOMETALLICS AS BIOMASS GASIFICATION CATALYSTS

FIELD OF THE INVENTION

The present invention relates to a method for improving the efficiency and output of a biomass gasification process. By the present disclosure, a volatile organometallic compound(s) is contacted with biomass before and/or during a gasification process. The subject disclosure provides a method to increase gas yields, reduce residual tar produced by gasification, produce methanol in situ, and otherwise improves a gasification process.

BACKGROUND OF THE INVENTION

Gasification is a process for converting carbonaceous materials into carbon monoxide and hydrogen by reacting the raw material at high temperatures with a limited but measured amount of oxygen and/or steam. If the biomass is naturally sufficiently oxygenated, then no oxygen and/or steam need be utilized in the gasification. The resulting mixture of carbon monoxide and hydrogen gas is known as synthesis gas or syngas. Basically, gasification is a method for extracting energy from different types of organic materials. The resulting syngas may be a more efficient combustion source than the original material.

The syngas can be used directly for energy production. Syngas is also used, via additional processing, to produce methanol and hydrogen or is converted via the Fischer-Tropsch process into a synthetic fuel, such as synthetic biodiesel. Gasification can also begin with materials that are not otherwise useful as fuels. For example, bio-mass/organic waste can be used as the feed material.

The amount of energy introduced to the gasification process is a major expense that subtracts from the net power production from the syngas. There is also an environmental impact to producing the required energy for gasification. On the other hand, biomass gasification and combustion is a potentially renewable energy that is $CO_2$ neutral. That is, biomass gasification can remove the same amount of $CO_2$ from the atmosphere as is emitted from gasification and combustion.

There is a need for improvements to the chemical biomass gasification process. Ideally, such improvements would improve gas yield, reduce tar production, and otherwise produce an improved gasification process for biomass. In addition, for the portion of the gasification product that results in a liquid product, an improved gasification process should ideally produce methanol to create a more stable liquid product.

SUMMARY OF THE DISCLOSURE

The method of the present disclosure provides for improved gasification of biomass including higher gas yields, reduced solid yields (including reduced tar production), and reduced liquid yields. The method comprising contacting the biomass with volatile organometallic compounds, such as MMT, CMT, ferrocene, or the like, before and/or during the gasification process. In addition, the volatile organometallics interact with lignin in the biomass to produce methanol, which, in turn, results in a stable liquid and/or oil product from the gasification. In addition, the resulting methanol can be captured and used or further processed By the subject method, biomass gasification leads to increased syngas production relative to gasification conducted without the subject method. The gasification process is potentially $CO_2$ neutral.

The subject method also provides the increased gas yields at lower temperatures. As such, there is an overall reduction in energy input while providing the increased gas yields. The reduction in energy reduces the cost and environmental impact associated with the gasification process.

With respect to increased gas yields, it has been surprisingly discovered that volatile organometallic compounds improve total gas yield from 41.5% at 450° C. (gasification without the compound) up to 63.41% at 400° C. at a treat rate of 4% of the organometallic compound by mass of the biomass. A treat rate of 1% of the organometallic compound by mass of the biomass increases gas yields from 41.5% at 450° C. to 53.94 at just 400° C. Conventionally, higher gasification reaction temperatures are employed in order to achieve higher gas yields. However, increased energy input is very expensive and incurs a corresponding, negative environmental impact (i.e., more fuel consumed to produce higher input temperatures). The subject method surprisingly provides increased gas yields at reduced reaction temperatures.

Biomass mainly comprises sugars, carbohydrates, cellulose lignin, water and minerals. It has been found that the volatile organometallics, while they do not cleave and depolymerise the lignin, nevertheless are able to cleave the methoxy groups on the lignin monomers (i.e., the molecules that combine to form the lignin polymer). Cleaving the methoxy group on guaiacyl and syringyl monolignols in wood lignins results in methanol production.

As demonstrated below, the volatile organometallic compounds useful in the present disclosure are very active on the carbohydrates in the biomass. In other words, the volatile organometallics very efficiently gasify carbohydrates (sugars, starches, and cellulose). The subject organometallic compounds interact with the organics in such a way as to reduce the formation of tars resulting from gasification. Decreased tar yields lead to increased gas yields. Tars/solids also clog gasification reactors or systems. The reactors must be taken offline to periodically clean the tar. As such, the reduction of tar or solid product by the present disclosure has several advantages.

The present disclosure further relates to a method that improves (decreases) liquid yields. Yet some liquid and/or oil production is inevitable. From the subject method, the resulting liquids, due to the production of methanol, are also more stable than liquids/oils produced by biomass gasification without the addition of the subject organometallic compounds.

By "organometallic compounds" herein is meant any molecules containing a carbon-metal moiety. These compounds may be "volatile" in that they can sublime or vaporize from ambient conditions up to about 450° C. Therefore, volatile organometallics could be, for example and without limitation, cyclomatic manganese carbonyl compounds such as methyl cyclopentadienyl manganese tricarbonyl, cyclopentadienyl manganese tricarbonyl, manganese carbonyl materials; ferrocene and iron carbonyl materials; cerium-containing compounds; platinum group metal compounds; and the like or mixtures thereof.

The organometallic compound(s) of the subject method is oil-soluble or dispersed or mixed in a lubricant, carrier fluid, or fuel. The compound could be in liquid or solid states. The subject organometallic compounds are contacted with the biomass before and/or during the gasification process. The compound can act within the reactor or at any point after the reaction products exit the gasification reactor or both. In other words, the organometallic compound can volatilize and thereby be injected into the gasification reactor or product (e.g., syngas) stream leaving the reactor.

By "biomass" herein is meant wild, anthropomorphically cultivated, genetically engineered, and/or bioengineered trees, bushes, grasses, algae, plankton, aquatic plants, yard trimmings and waste, wood chips, saw dust, mariculture products, animal parts and carcasses, animal waste, farm waste, agricultural waste, fodder, silage, organic waste and/or by-products and mixtures thereof alone or in combination with emulsions, suspensions, and dispersions thereof in water, alcohol, or other carrier fluids. 'Biomass' is broadly intended to mean woods, grasses, aquatic life, and/or animals or animal by-products/waste. In yet a further embodiment, "biomass" comprises coal, coal dust, and the like. In at least one embodiment, biomass is a renewable fuel source.

By "contacting" herein is meant the contacting, bringing together, reacting, complexing, coordinating, combining, admixing, mixing, and the like association between two or more materials, whether or not a chemical or physical reaction or change occurs.

It is to be understood that both the foregoing general description and the following detailed description are exemplary and explanatory only and are intended to provide further explanation of the present invention, as claimed. The foregoing and additional features and advantages of the present invention will become apparent to those of skill in the art from the following detailed description of a preferred embodiment taken in conjunction with the accompanying drawings.

BRIEF DESCRIPTION OF THE FIGURES

FIG. 2 illustrates one volatile organometallic compound as a biomass gasification catalyst at various treat rates and temperature compared to a baseline result without the organometallic compound(s) at 450° C.; and FIGS. 3-6 illustrate $^{13}$C-NMR spectrum analysis of the resulting bio-oil resulting from the gasification of biomass with and without the subject organometallic compounds.

DETAILED DESCRIPTION OF THE DISCLOSURE

Figure 1:
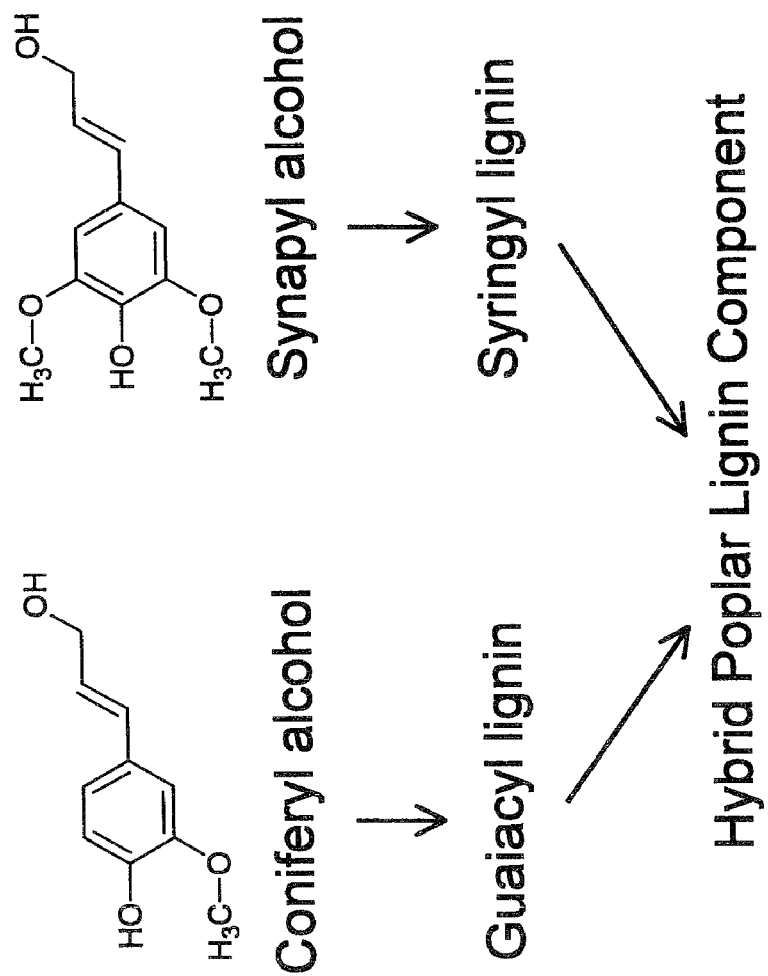
FIG. 1 illustrates the guaiacyl and syringyl monomers of the heteropolymer lignin backbone in a hybrid poplar biomass wherein methoxy groups are cleaved via an organometallic or volatile organometallic introduced before and/or during biomass gasification, as taught by the subject disclosure, to give rise to methanol.

In further detail, the presently disclosed method provides biomass gasification with increased gas yields and reduced solid and liquid yields at lower temperatures than conventionally used. The method comprises contacting a volatile organometallic compound with the biomass before or during gasification.

Based on data provided below, it is apparent the volatile organometallic compounds increase gas yields of the biomass gasification. In one embodiment, the amount of the volatile organometallic compound(s) provided to the biomass is greater than 1% by mass of the total mass of the biomass. In another embodiment, the organometallic compound is provided at 1% to 4% by mass of the total mass of the biomass.

In a further embodiment of the present invention, it is contemplated that the volatile organometallic compound is methyl cyclopentadienyl manganese tricarbonyl, which is combined at 0.5 to 10 weight percent with the biomass (i.e., by mass of the biomass). In this embodiment, the biomass includes wood chips. The biomass and organometallic compound are fed into a gasifier combustion unit containing a heating medium, are fluidized with a flowing gas including nitrogen, and are heated to a temperature of from 300 degrees Centigrade to 800 degrees Centigrade to produce a gasification product. In another embodiment, the organometallic compound includes methyl cyclopentadienyl manganese tricarbonyl and is present in a resulting biomass plus organometallic compound mixture at a weight ratio of greater than 1%.

The improvement in the gasification efficiency can, in one embodiment, be measured by increased gas yields. A baseline test was conducted where the organometallic compound treatment of the present disclosure was not employed. The baseline test was conducted at one conventional, minimum gasification temperature of 450° C. In accordance with the present disclosure, a sample gasification reaction was conducted at a reduced temperature of 400° C. in the presence of 1% organometallic compound by mass of the biomass. Gas yields increased from the baseline of 41.5% to 53.94%. The percent change increase in yields, despite the reduction in energy, is 29.98% relative to the gas yield from the gasification of comparable biomass without an organometallic compound where the gasification was conducted at 450° C. For a 4% treat rate, the percent change increase in yields is 52.80%.

Applicant expects that were the tests with the organometallic compound conducted at the same temperature as the baseline test without the organometallic compound(s), the increase in yield would have been even greater. As such, the increase in gas yields from at least one embodiment of the presently disclosed method is, at a minimum, 29.9%.

The gasification by the subject method is also more efficient in that liquid yields are decreased. As disclosed further below, liquid yields from a gasification process without the organometallic compounds at 450° C. accounted for 43.7% of the gasification product. When the gasification is conducted with 1% of an organometallic compound by mass of the biomass at 400° C., the liquid yield is reduced to 34.75%. The percent change decrease in yields, despite the reduction in energy, is 20.48%.

Likewise, tar and solid yields are reduced. The baseline gasification process produced 14.9% char/solids as a product of the gasification. When the gasification is conducted with 1% of an organometallic compound by mass of the biomass at 400° C., the char/solid yield is reduced to 11.35%. The percent change decrease in the gasification efficiency is measured by decreased solid yields of at least 23.83%.

The improved gas yields and methanol production of the subject method are thought to be provided at any gasification temperature while the data below was compiled at 400, 600 and 800° C. The increased gas yields via the organometallic compound(s) are particularly provided at lower gasification temperatures in the range of 300 to 600° C. Nevertheless, volatile organometallics compounds were found to be active all the way to a tested peak of 800° C. and are expected to be active above the tested peak.

The volatile organometallic compound(s) work on volatile organics in the biomass. The compound(s) does cleave methoxy on guaiacyls and syringyl monolignols. Consequently, while methanol is not typically produced by biomass gasification in any substantial quantity, the subject method does provide methanol in situ via these cleaved methoxy substituents on the aromatic rings of materials in the biomass.

It is known that some oil production from gasification is expected. One gasification technique that produces oil is involves two steps: 1) pyrolysis to give bio-oils, char, and gases, and 2) subsequent gasification of the char and bio-oils.

The bio-oil product(s) may be separated to be further worked/processed into value added products such as pharmaceuticals, thermoplastics, etc.

The methanol produced in situ by the subject method keeps the oil from thickening (i.e., the methanol acts a stabilizer). Without methanol, the oil is more likely to solidify, making it difficult to process as described above. Reversing the oil from a solid requires additional processing, which is more expensive and consumes even more energy. In addition to stabilizing the oil or liquid product, the methanol is recoverable as a product of the gasification either as a component of the liquid, isolated, processed, or the like. The recovered methanol can be processed further or used as a fuel source.

The above reaction is further illustrated in FIG. 1. Namely, the monomers that form guaiacyl and syringyl lignin components of the lignin structure contain methoxy groups that are cleaved by the organometallic compound. For this illustration, and in the test below, the biomass comprised hybrid poplar chips.

With respect to the table of FIG. 2, there is illustrated therein the performance of one volatile organometallic compound as a biomass gasification catalyst. Namely, FIG. 2 discloses the "baseline" biomass gasification test with no organometallic compound included. As noted above, the "baseline" results were observed at a gasification process conducted at 450° C. The resulting oil yield is 43.70%. The char (solid) yield is 14.90% with an observed gas yield of 41.50%.

In accordance with the presently disclosed method, a volatile organometallic compound was added to the biomass at a treat rate of 1% of the total biomass mass. For this example, the organometallic compound comprised methylcyclopentadienyl manganese tricarbonyl (as sold under the brand name HiTEC® 3000 Fuel Additive). The gasification process was then conducted at 400° C. Oil yields fell from 43.7% at 450° C. and no organometallic compound(s) to 34.7% with the introduction of 1% organometallic compound by mass of the biomass at 400° C. Char/solid yields were reduced from 14.9% to 11.35% under respective conditions. Finally, gas yields unexpectedly rose from 41.5% to 53.94%. It is thought that an even more improved yield spread would be obtained if the testing between the gasification without the organometallics and the testing with the organometallic were conducted at the same temperature. Therefore, the minimum percent increase for this embodiment of the subject method is thought to be 29.98%.

The table of FIG. 2 also illustrates a biomass gasification process conducted with 4% methylcyclopentadienyl manganese tricarbonyl by weight. Relative to the "baseline" test (i.e., 450° C. and no organometallic compound(s)), oil yields fell from 43.7% to 25.50%. Char yields fell from 14.9% to 11.09%. Gas yields dramatically and unexpectedly increased from the 41.5% baseline to 63.41%. The lower temperature input (400° C. for gasification with the organometallic compound compared to 450° C. for the baseline test without the organometallic compound) reduces costs and the environmental impact of producing the energy necessary to conduct the gasification process.

Again, the difference between baseline gas yields and gas yields produced by the subject method at 400° C. would be even greater if the respective testing was conducted at the same temperature as opposed to the baseline sample at 450° C. In one embodiment of the subject method, the percentage increase in gas yield with a 4% organometallic treat rate is at least 52.78%

The biomass for these experiments was hybrid poplar chips that were ground then sieved through a 28-mesh (595 micro) sieve. The biomass was pre-treated with the volatile organometallic material before the biomass was screw fed into the entrainment zone of the gasifier at a rate of 90 to 100 g/h. The gasifier contained 100 g silica gel (−28 to +60 mesh) as the heating medium. A gas comprising nitrogen was added at flow rate of 18 L/min. The organometallic compound was in a liquid state at ambient temperatures, although the organometallic could be a solid, dispersion, etc. The organometallic compound ideally contacts multiple points of the biomass during a pre-treatment of the biomass (i.e., before feeding the biomass into the reactor). The organometallic compound(s) might also be directly injected into the reactor during the reaction. In any event, the organometallic compound is volatile in that it sublimes or vaporizes above ambient conditions and below the temperature of the gasification reactor. After sublimation or vaporization, the organometallic compound can also enter the product (syngas) stream While gasification produces hydrogen gas, the increased gas yield provided by the method disclosed herein is mainly partitioned between CO and $CO_2$ (components of syngas). Much of the $CO_2$ comes from the catalytic decarboxylation of carboxyl functional groups in the biomass. $CO_2$ can be optionally converted to the more desired CO product by a water gas shift reaction component.

A detailed analysis of the liquid product revealed that the organometallic compound(s)s of the subject method efficiently process carboxylates and oxygenated 1o substituents in the biomass. This is evident in the carbon nuclear magnetic resonance spectroscopy (aka, $^{13}$C-NMR or C-NMR) as illustrated in FIGS. 3-6. With respect to FIG. 3, there is illustrated the $^{13}$C-NMR spectrum of a bio-oil produced by the above gasification process without an organometallic compound(s) where the gasification is conducted at 450° C. The resonance spike at 49.7 corresponds with methanol in the bio oil, as labeled in the graph.

Turning to FIGS. 4-6, the highest activity of the organometallic compound(s) is in the $^{13}$C-NMR range of 60-102 ppm, as labeled on the graph. The indicated range comprises carbohydrate decomposition products, mostly levoglucosan and hydroxyacetaldehyde. As noted above, the subject organometallic compounds also effectively cleave methoxy substituents on the biomass lignins to yield methanol. This is indicated in the $^{13}$C-NMR resonance spike at 49.7 ppm with corresponding $^{13}$C-NMR spectral intensity decreases in the $^{13}$C methoxyl bands associated with 55, 56 and 57 ppm peaks. The specific methoxylated biomass aromatic heteropolymers being cleaved to yield methanol are syringyl and guaicyl lignins, as discussed above. The organometallic compound effects on carbohydrates and methanol production increases as input temperature increases to 600 degrees C. and 800 degrees C. (see FIGS. 5 and 6).

As such, the subject disclosure provides a method to produce methanol from a biomass gasification process. In one embodiment of the method, the steps to produce methanol comprise contacting one or more organometallic compounds with a biomass before and/or during a gasification process of the biomass. Methoxy substituents are cleaved from the aromatic rings of materials in the biomass via the organometallic compound(s) to yield methanol. Optionally, the methanol that is produced may be recovered as a product of the gasification. In another embodiment, the aromatic rings of materials in the biomass are selected from lignin heteropolymer backbones derived from guaiacyl and syringyl monomers.

As the organometallic compound is unexpectedly active with organics that would otherwise contribute to the formation of tars, the overall solid yields are reduced. Tars from gasification also clog the reactor or gasification system and lead to down time for the gasification reactor (cleaning/repair). A reduction in tar production reduces clean-up and down time.

The subject method produces increased syngas, including carbon monoxide, relative to gasification of a biomass that is not in accordance with the subject method. Carbon monoxide production from biomass is accomplished by contacting an organometallic compound(s) with a biomass before or during gasification of the biomass. The biomass comprises components having carbonyl and hydroxyl functional groups. The organometallic compound(s), during gasification, cause the catalytic decarbonylation of carbonyl functionalities, derived from ketonyl and aldehydic functional groups, and carbonyl functionalities, from oxidation of hydroxyl groups to ketonyl and aldehydic functional groups, and the decarboxylation of carboxyl functional groups. The decarbonylation/decarboxylation of these functional groups/functionalities produces a mixture of gases. The mixture includes carbon monoxide, carbon dioxide, and hydrogen. As noted above, $CO_2$ can be optionally converted to the more desired CO product by a water gas shift reaction component.

It is therefore believed that the use of the subject method provides significant and unexpected benefits for the gasification process of biomass. The subject method increases gas yields, reduces solid and liquid yields and provides a means to produce methanol in situ. Carbon monoxide is produced, and methanol can also be collected after the gasification. Tar production is reduced. The subject method will produce a dramatic and highly desirable benefit for processes, devices and systems for the gasification of biomass.

Other embodiments of the present invention will be apparent to those skilled in the art from consideration of the specification. It is intended that the specification and Figures be considered as exemplary only, with a true scope and spirit of the invention being indicated by the following claims.

What is claimed is:

1. A method for improving the efficiency of biomass gasification process, said method comprising contacting a volatile organometallic compound with said biomass before or during gasification of said biomass wherein the volatile organometallic compound is selected from the group consisting of cyclomatic manganese carbonyl compounds, methyl cyclopentadienyl manganese tricarbonyl, cyclopentadienyl manganese tricarbonyl, manganese carbonyl materials, ferrocene, iron carbonyl materials, cerium-containing compounds, platinum group metal compounds, and mixtures thereof, and wherein the biomass gasification process comprises converting said biomass into carbon monoxide and hydrogen by reacting said biomass with at least one of oxygen and steam, wherein the volatile organometallic compound comprises between 1 to 10% by mass of the biomass, wherein a gasification temperature is from 300 to 800 degrees Centigrade, and wherein the improvement in the gasification efficiency is measured by an increase in gas yields of at least 29.9% relative to the gas yield from the gasification of comparable biomass without an organometallic compound at 450 degrees Centigrade.

2. The method of claim 1, wherein the biomass is selected from the group consisting of wild and/or anthropomorphically cultivated, and/or genetically engineered, and/or bioengineered trees, bushes, grasses, algae, plankton, aquatic plants, animals, yard trimmings and waste, wood chips, saw dust, mariculture products, animal parts and carcasses, animal waste, farm waste, agricultural waste, fodder, silage, organic waste and/or by-products, and mixtures thereof, and emulsions, suspensions, and dispersions thereof in water, alcohol, or other carrier fluids.

3. The method of claim 1, wherein the biomass is selected from a group comprising coal, coal dust, and mixtures thereof, and emulsions, suspensions, and dispersions thereof in a carrier fluid.

4. The method of claim 1, wherein the volatile organometallic compound is methyl cyclopentadienyl manganese tricarbonyl, wherein the biomass comprises wood chips, wherein the biomass and organometallic compound are fed into a gasifier combustion unit containing a heating medium, fluidized with a flowing gas comprising nitrogen, and heated to a the gasification temperature of from 300 degrees Centigrade to 800 degrees Centigrade, whereby gasification product is produced.

5. The method of claim 1, wherein the volatile organometallic compound comprises a carbon-metal moiety that sublimes or vaporizes at temperatures from ambient up to about 450° C.

6. The method of claim 1, wherein the volatile organometallic compound is at least one of oil-soluble, dispersed in at least one of a lubricant, carrier fluid, or fuel, or mixed in at least one of a lubricant, carrier fluid, or fuel.

7. The method of claim 1, wherein the gasification temperature is between 300 to 600 degrees Centigrade.

8. The method of claim 7, wherein the volatile organometallic compound comprises between 1 to 4% by mass of the biomass.

9. The method of claim 8, wherein the volatile organometallic compound comprises 1% by mass of the biomass.

10. The method of claim 8, wherein the volatile organometallic compound comprises 4% by mass of the biomass.

11. The method of claim 7, wherein the gasification temperature is 400 degrees Centigrade.

12. The method of claim 11, wherein the volatile organometallic compound comprises between 1 to 4% by mass of the biomass.

13. The method of claim 12, wherein the volatile organometallic compound comprises 1% by mass of the biomass.

14. The method of claim 13, wherein the improvement in the gasification efficiency is measured by a percent change increase in gas yields of at least 29.98% relative to the gas yield from the gasification of comparable biomass without an organometallic compound at 450 degrees Centigrade.

15. The method of claim 13, wherein the improvement in the gasification efficiency is measured by percent change decrease of liquid yields of at least 20.48% relative to the liquid yield from the gasification of comparable biomass without an organometallic compound at 450 degrees Centigrade.

16. The method of claim 13, wherein the improvement in the gasification efficiency is measured by a percent change decrease of solid yields of at least 23.83% relative to the solid yield from the gasification of comparable biomass without an organometallic compound at 450 degrees Centigrade.

17. The method of claim 12, wherein the volatile organometallic compound comprises 4% by mass of the biomass.

18. The method of claim 17, wherein the improvement in the gasification efficiency is measured by a percent change increase in gas yields of at least 52.78% relative to the gas yield from the gasification of comparable biomass without an organometallic compound at 450 degrees Centigrade.

19. The method of claim 17, wherein the improvement in the gasification efficiency is measured by percent change decrease of liquid yields of at least 41.65% relative to the liquid yield from the gasification of comparable biomass without an organometallic compound at 450 degrees Centigrade.

20. The method of claim 17, wherein the improvement in the gasification efficiency is measured by a percent change decrease of solid yields of at least 25.57% relative to the solid yield from the gasification of comparable biomass without an organometallic compound at 450 degrees Centigrade.

21. The method of claim 7, wherein the gasification temperature is 600 degrees Centigrade.

22. The method of claim 21, wherein the volatile organometallic compound comprises between 1 to 4% by mass of the biomass.

23. The method of claim 22, wherein the volatile organometallic compound comprises 1% by mass of the biomass.

24. The method of claim 22, wherein the volatile organometallic compound comprises 4% by mass of the biomass.

25. The method of claim 23, wherein the improvement in the gasification efficiency is measured by a percent change increase in gas yields of at least 48.67% relative to the gas yield from the gasification of comparable biomass without an organometallic compound at 450 degrees Centigrade.

26. The method of claim 23, wherein the improvement in the gasification efficiency is measured by percent change decrease of liquid yields of at least 42.33% relative to the liquid yield from the gasification of comparable biomass without an organometallic compound at 450 degrees Centigrade.

27. The method of claim 23, wherein the improvement in the gasification efficiency is measured by a percent change decrease of solid yields of at least 12.75% relative to the solid yield from the gasification of comparable biomass without an organometallic compound at 450 degrees Centigrade.

28. The method of claim 1, wherein the gasification temperature is 800 degrees Centigrade.

29. The method of claim 28, wherein the volatile organometallic compound comprises between 1 to 4% by mass of the biomass.

30. The method of claim 29, wherein the volatile organometallic compound comprises 1% by mass of the biomass.

31. The method of claim 29, wherein the volatile organometallic compound comprises 4% by mass of the biomass.

32. The method of claim 30, wherein the improvement in the gasification efficiency is measured by a percent change increase in gas yields of at least 111.08% relative to the gas yield from the gasification of comparable biomass without an organometallic compound at 450 degrees Centigrade.

33. The method of claim 30, wherein the improvement in the gasification efficiency is measured by percent change decrease of liquid yields of at least 88.56% relative to the liquid yield from the gasification of comparable biomass without an organometallic compound at 450 degrees Centigrade.

34. The method of claim 30, wherein the improvement in the gasification efficiency is measured by a percent change decrease of solid yields of at least 56.38% relative to the solid yield from the gasification of comparable biomass without an organometallic compound at 450 degrees Centigrade.

35. A method to produce methanol from a biomass, the method comprising:
  contacting volatile organometallic compound with a biomass before and/or during a gasification process of said biomass;
  cleaving methoxy substituents on aromatic rings of materials in the biomass via the organometallic compound to yield methanol;
  and, optionally, recovering the methanol produced therefrom as a product of the gasification,
  wherein the volatile organometallic compound is selected from the group consisting of cyclomatic manganese carbonyl compounds, methyl cyclopentadienyl manganese tricarbonyl, cyclopentadienyl manganese tricarbonyl, manganese carbonyl materials, ferrocene, iron carbonyl materials, cerium-containing compounds, platinum group metal compounds, and mixtures thereof, and
  wherein the gasification process of said biomass comprises converting said biomass into carbon monoxide and hydrogen by reacting said biomass with at least one of oxygen and steam,
  wherein the volatile organometallic compound comprises between 1 to 10% by mass of the biomass,
  wherein a gasification temperature is from 300 to 800 degrees Centigrade, and
  wherein an improvement in gasification efficiency is measured by an increase in gas yields of at least 29.9% relative to the gas yield from the gasification of comparable biomass without an organometallic compound at 450 degrees Centigrade.

36. The method of claim 35, wherein the aromatic rings of materials in the biomass are selected from lignin heteropolymer backbones derived from guaiacyl and syringyl monomers.

37. A method to produce carbon monoxide from biomass, comprising the steps:
  (a) contacting volatile organometallic compound with a biomass before or during gasification of said biomass, wherein said biomass comprises components having carbonyl and hydroxyl functional groups;
  (b) causing the catalytic decarbonylation of carbonyl functionalities derived from ketonyl and aldehydic functional groups, carbonyl functionalities from oxidation of hydroxyl groups to ketonyl and aldehydic functional groups, and decarboxylation of carboxyl functional groups to produce a mixture of gases, the mixture including carbon monoxide, carbon dioxide, and hydrogen; and
  (c) optionally, converting the carbon dioxide to carbon monoxide by a water gas shift reaction,
  wherein the volatile organometallic compound is selected from the group consisting of cyclomatic manganese carbonyl compounds, methyl cyclopentadienyl manganese tricarbonyl, cyclopentadienyl manganese tricarbonyl, manganese carbonyl materials, ferrocene, iron carbonyl materials, cerium-containing compounds, platinum group metal compounds, and mixtures thereof, and
  wherein gasification of the biomass comprises converting said biomass into carbon monoxide and hydrogen by reacting said biomass with at least one of oxygen and steam,
  wherein the volatile organometallic compound comprises between 1 to 10% by mass of the biomass,
  wherein a gasification temperature is from 300 to 800 degrees Centigrade, and
  wherein an improvement in gasification efficiency is measured by an increase in gas yields of at least 29.9% relative to the gas yield from the gasification of comparable biomass without an organometallic compound at 450 degrees Centigrade.

38. The method of claim 37, wherein the components are selected from the group comprising levoglucosans and hydroxyacetaldehydes.

39. The method of claim 37, wherein the components are selected from the group comprising sugars, carbohydrates and carboxy phenols.

* * * * *